US011224564B2

(12) United States Patent
Lee et al.

(10) Patent No.: US 11,224,564 B2
(45) Date of Patent: Jan. 18, 2022

(54) COMPOSITION COMPRISING ERIGERON ANNUUS FLOWER ESSENTIAL OIL FOR PREVENTION AND TREATMENT OF NEUROMUSCULAR DISEASE

(71) Applicant: HOSEO UNIVERSITY ACADEMIC COOPERATION FOUNDATION, Asan-si (KR)

(72) Inventors: Hwan-Myung Lee, Cheonan-si (KR); Dae-Il Hwang, Gumi-si (KR); Do-Yoon Kim, Hwaseong-si (KR); Soo-Min Park, Siheung-si (KR); Ha-Bin Kim, Cheonan-si (KR)

(73) Assignee: HOSEO UNIVERSITY ACADEMIC COOPERATION FOUNDATION, Asan-si (KR)

( * ) Notice: Subject to any disclaimer, the term of this patent is extended or adjusted under 35 U.S.C. 154(b) by 0 days.

(21) Appl. No.: 16/635,423

(22) PCT Filed: Sep. 11, 2018

(86) PCT No.: PCT/KR2018/010592
§ 371 (c)(1),
(2) Date: Jan. 30, 2020

(87) PCT Pub. No.: WO2020/004709
PCT Pub. Date: Jan. 2, 2020

(65) Prior Publication Data
US 2021/0085588 A1 Mar. 25, 2021

(30) Foreign Application Priority Data

Jun. 29, 2018 (KR) .......................... 10-2018-0075159

(51) Int. Cl.
| | |
|---|---|
| *A61K 36/28* | (2006.01) |
| *A61Q 19/00* | (2006.01) |
| *A61K 8/64* | (2006.01) |
| *A61K 8/92* | (2006.01) |
| *A61K 38/48* | (2006.01) |

(52) U.S. Cl.
CPC .................. *A61K 8/64* (2013.01); *A61K 8/92* (2013.01); *A61K 36/28* (2013.01); *A61K 38/48* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 5,721,215 | A | * | 2/1998 | Aoki ....................... A61P 21/02 514/17.7 |
| 2005/0196414 | A1 | * | 9/2005 | Dake ....................... A61P 43/00 424/239.1 |
| 2012/0107431 | A1 | | 5/2012 | Kim et al. |
| 2016/0151467 | A1 | | 6/2016 | Choi et al. |
| 2017/0143808 | A1 | | 5/2017 | Kleiner-Fisman |

FOREIGN PATENT DOCUMENTS

| | | | |
|---|---|---|---|
| CN | 101015577 A | | 8/2007 |
| JP | 2012-532097 A | | 12/2012 |
| JP | 2015172017 | * | 1/2015 |
| JP | 2015172017 | * | 10/2015 |
| KR | 10-0913917 B1 | | 8/2009 |
| KR | 10-2011-0001915 A | | 1/2011 |
| KR | 10-1262557 B1 | | 5/2013 |
| KR | 10-2015-0144735 A | | 12/2015 |
| KR | 10-2017-0007859 A | | 1/2017 |
| KR | 1020180051821 A | | 5/2018 |
| WO | 2011002179 A2 | | 1/2011 |

OTHER PUBLICATIONS

New Directions Aromatics, Untapping the Power of Nature: Essential Oil Extraction Methods, https://www.newdirectionsaromatics.com/blog/articles/how-essential-oils-are-made.html, Mar. 20, 2017 (Year: 2017).*
Development of Natural Material for Botox from Annual Feabane Yonhapnews, Aug. 13, 2018, 3 pages.
International Search Report of PCT/KR2018/010592 dated Mar. 26, 2019.
Communication dated Feb. 16, 2021, from the Japanese Patent Office in application No. 2020-529082.
Communication (EESR) dated Jul. 2, 2021, from the European Patent Office for related European Patent Application No. 18924465.0.

* cited by examiner

Primary Examiner — Jennifer A Berrios
(74) Attorney, Agent, or Firm — Sughrue Mion, PLLC

(57) ABSTRACT

Disclosed are a pharmaceutical composition and a beauty-purposed pharmaceutical composition for prevention or treatment of neuromuscular disease, the composition including a combination of Erigeron annuus flower-based essential oil and Botox. Erigeron annuus flower-based essential oil inhibits t-SNARE protein and v-SNARE protein expression in neurons to inhibit the formation of SNARE protein complexes. Erigeron annuus flower-based essential oil inhibits the regeneration of t-SNARE protein and v-SNARE protein degraded by Botox to inhibit neurotransmitter release. Accordingly, an efficacy duration of Botox may be extended. Thus, Erigeron annuus flower-based essential oil may be usefully used in combination with Botox as Botox adjuvant for the prevention and treatment of neuromuscular disease or for beauty.

3 Claims, 13 Drawing Sheets

[FIG. 1]
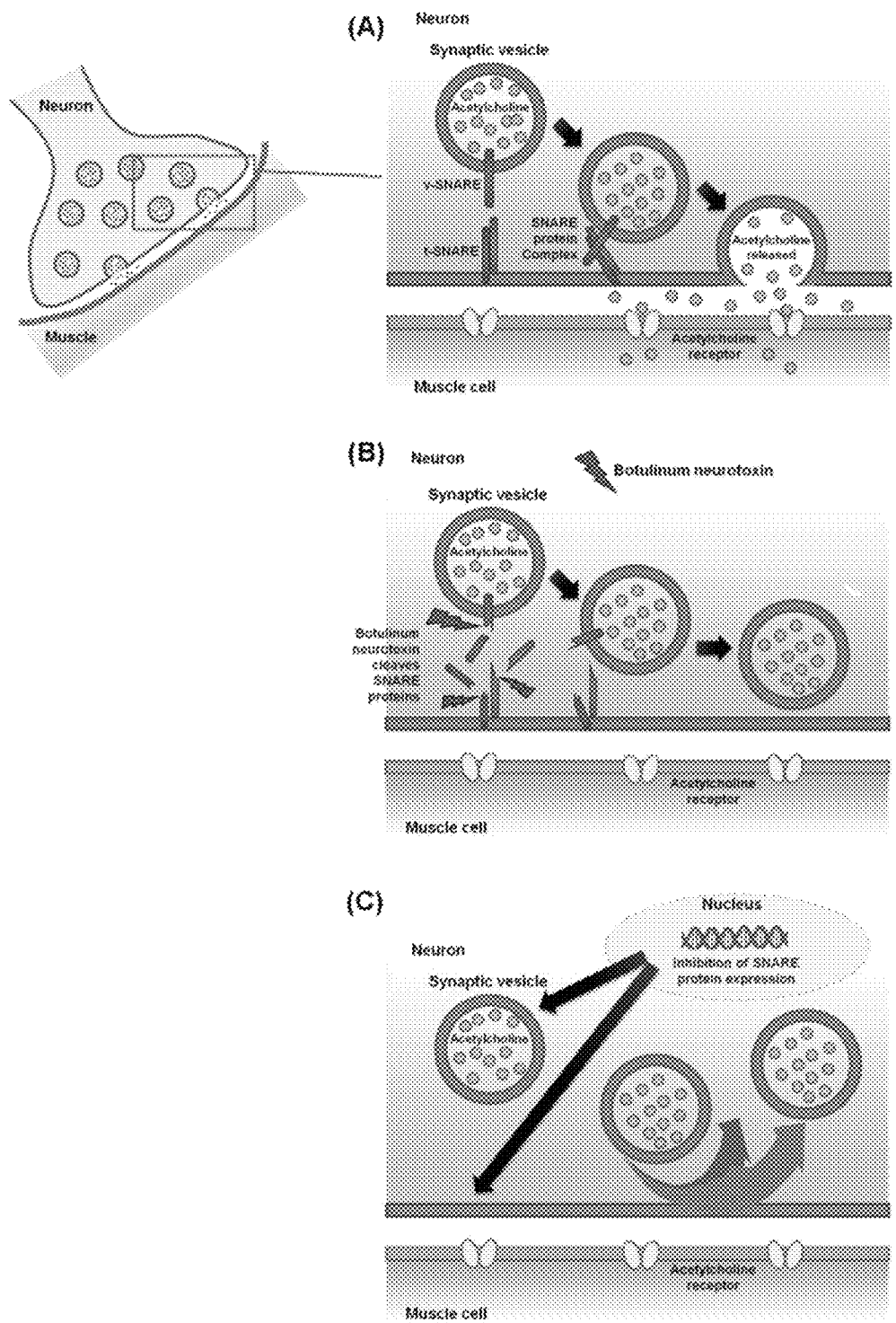

[FIG. 2]
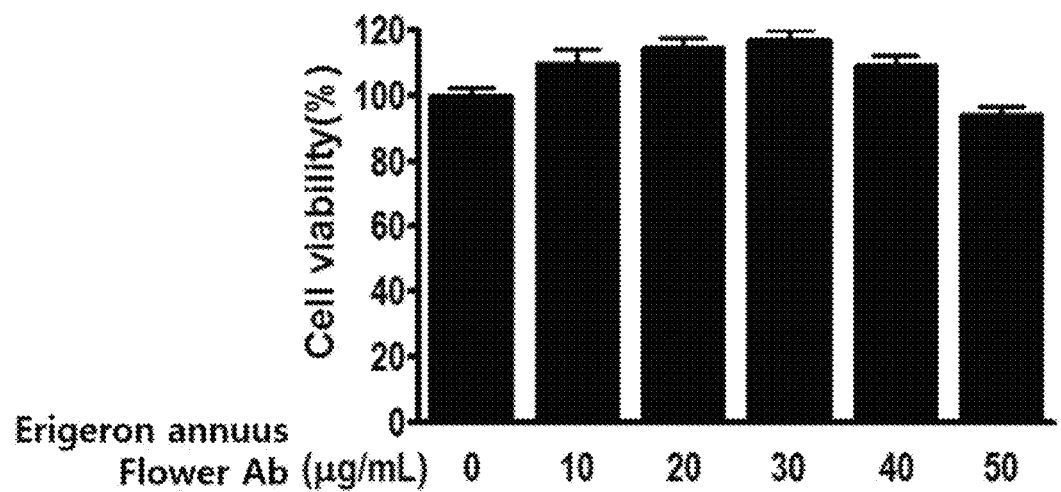

[FIG. 3]
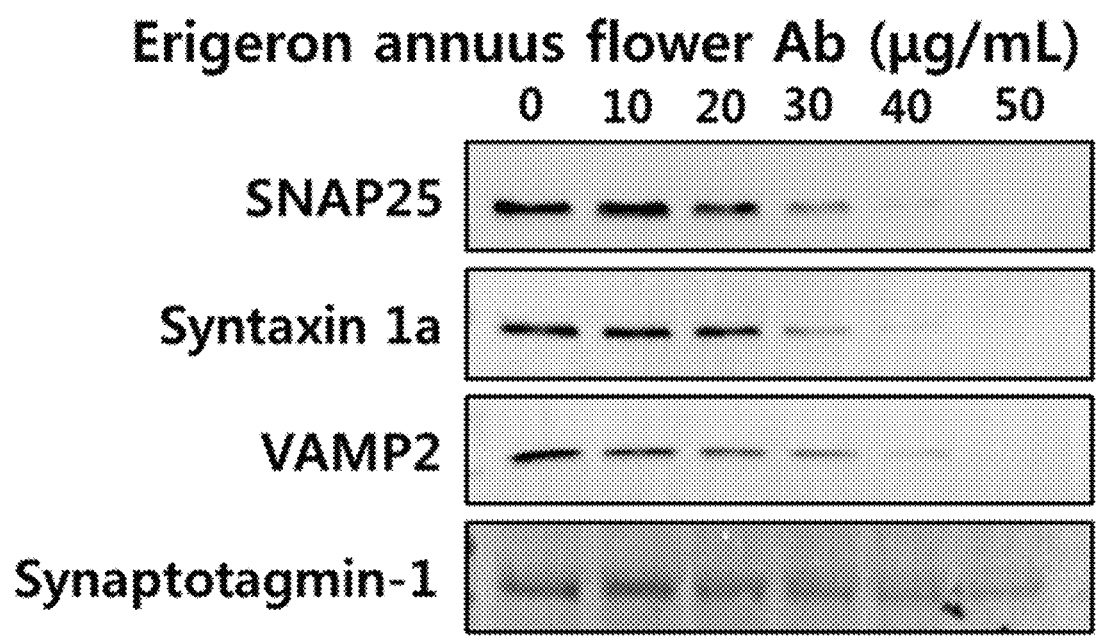

[FIG. 4]
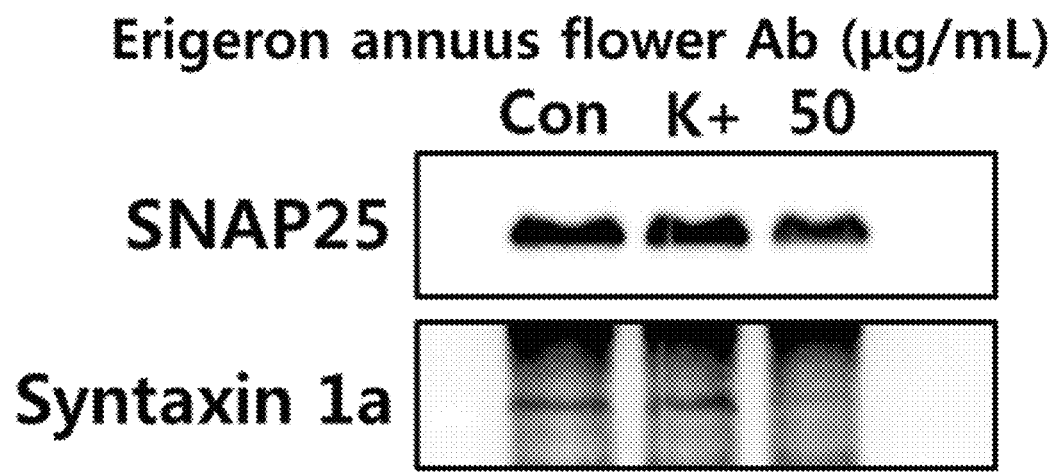

[FIG. 5]
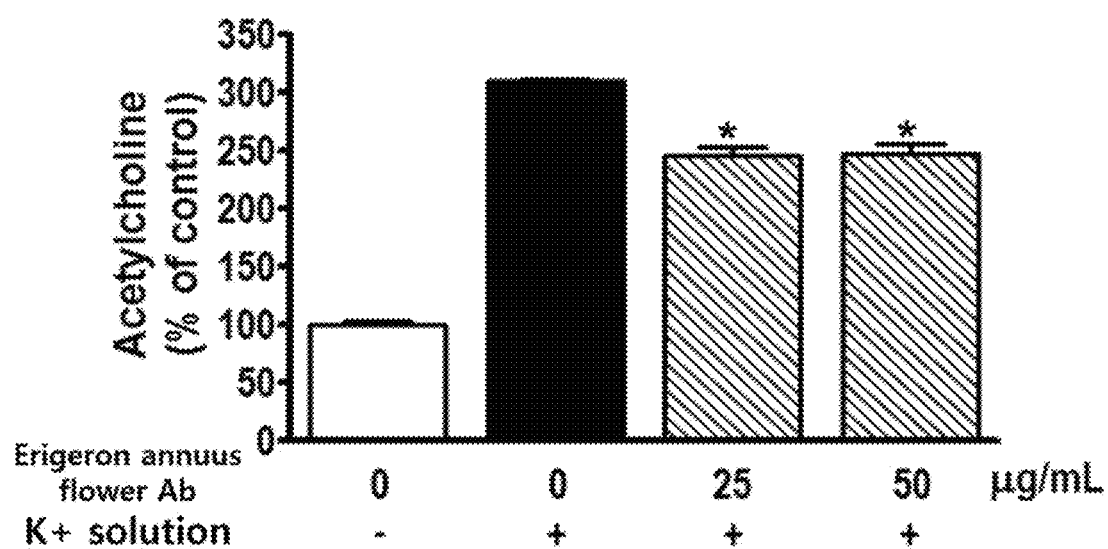

[FIG. 6]
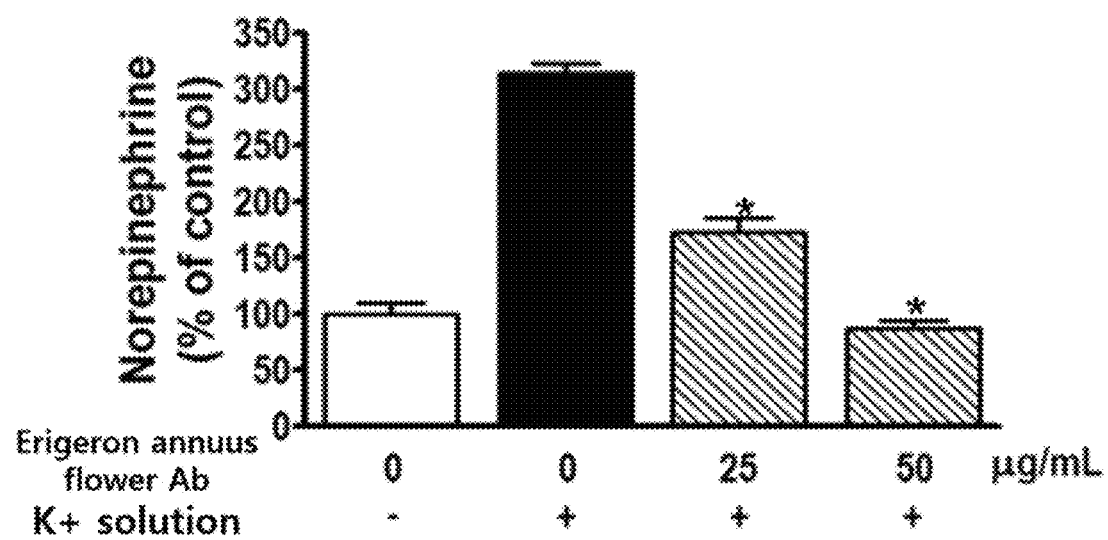

[FIG. 7]
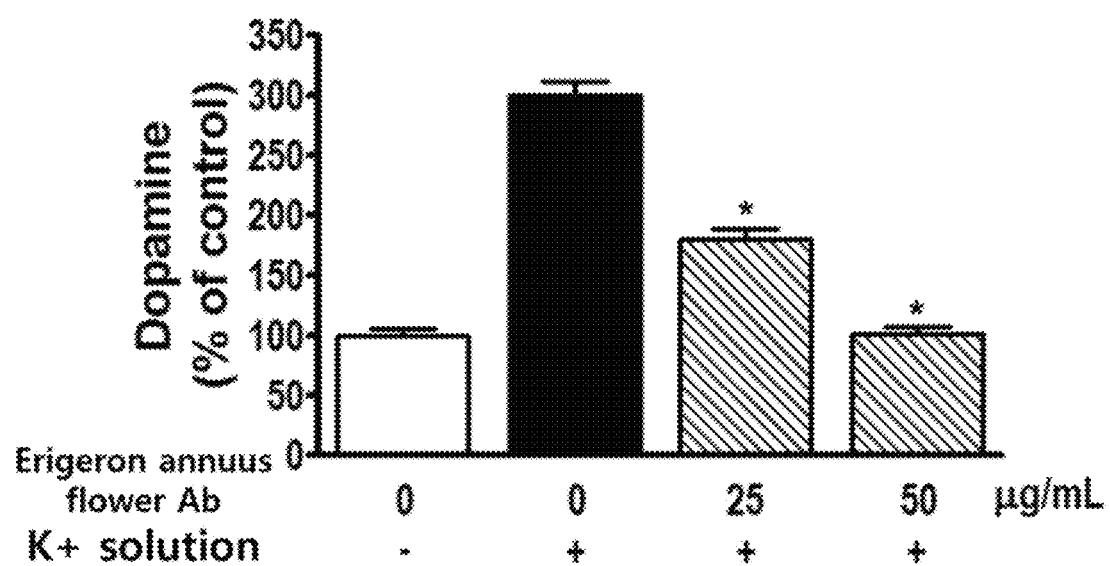

[FIG. 8]
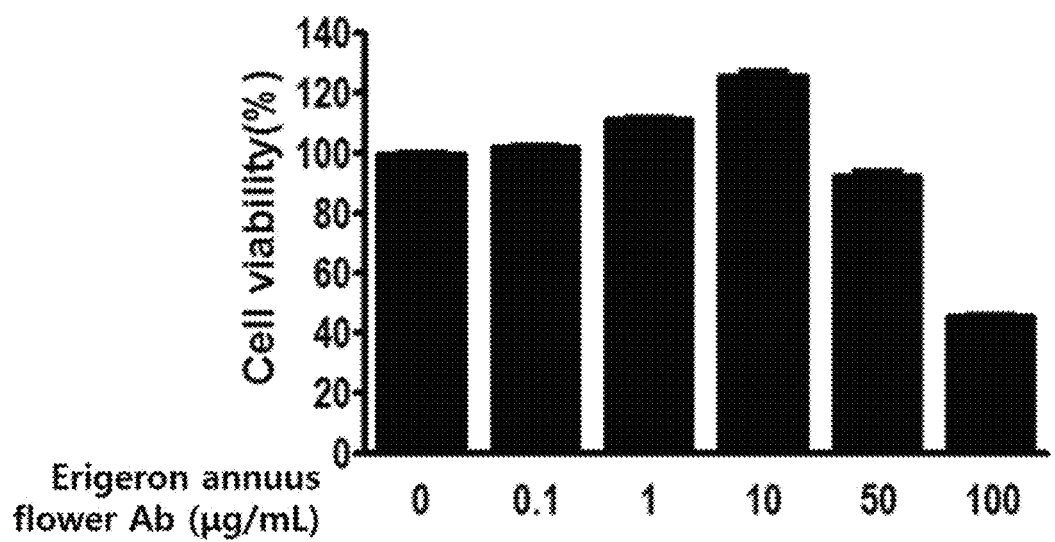

[FIG. 9]
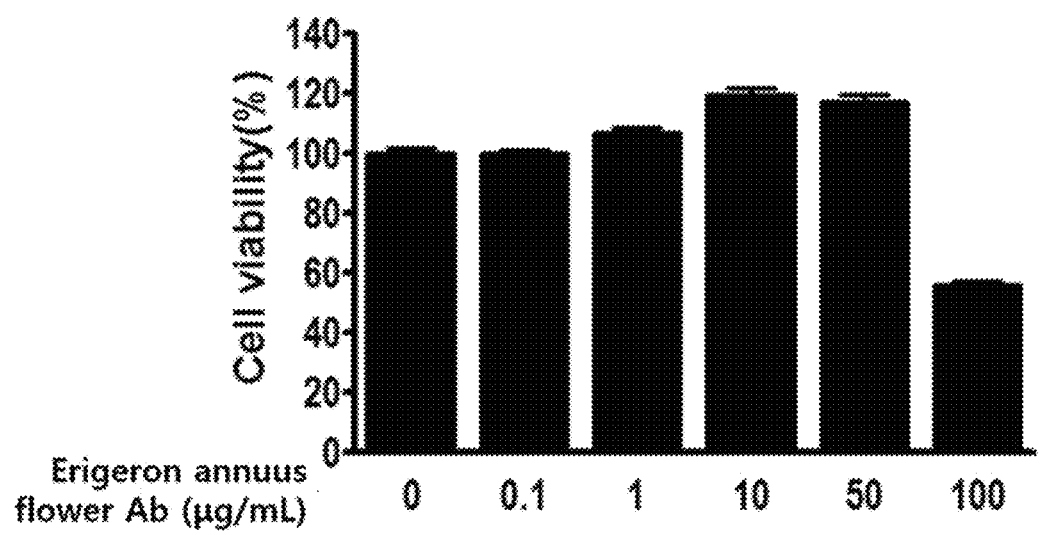

[FIG. 10]
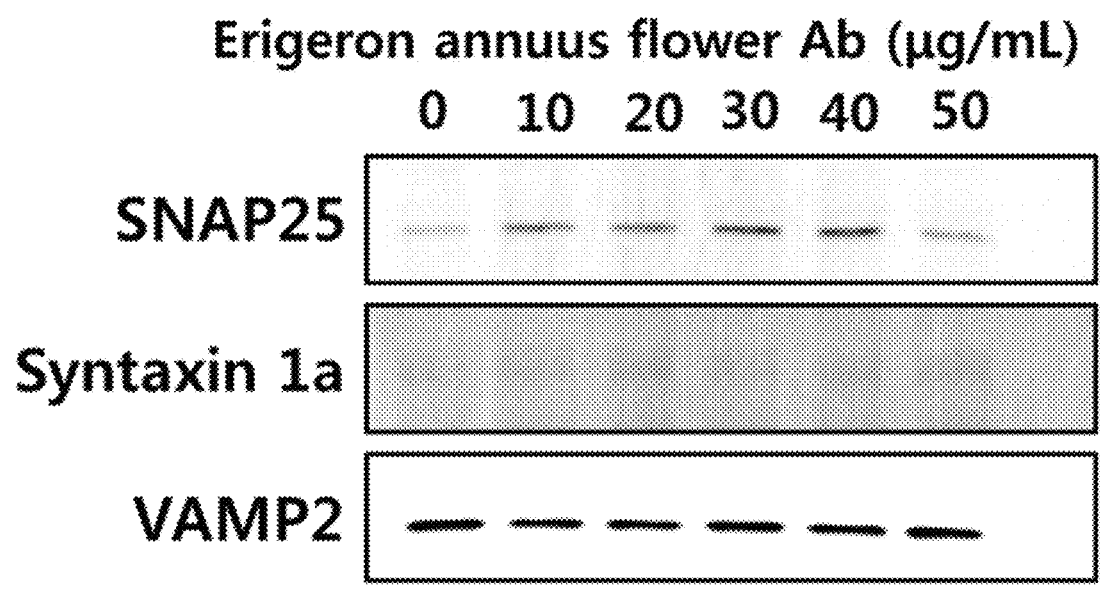

[FIG. 11]
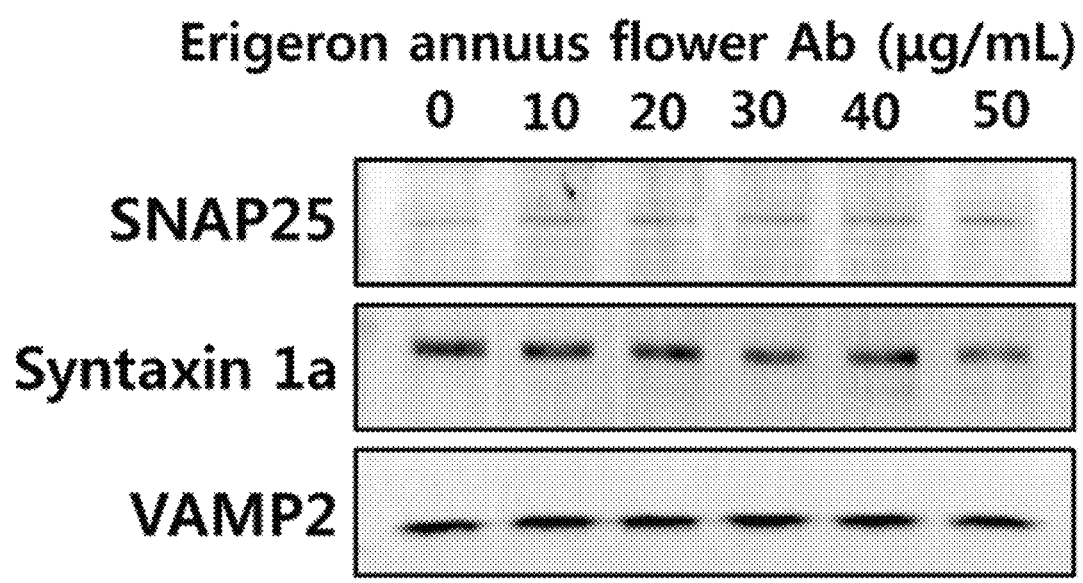

[FIG. 12]
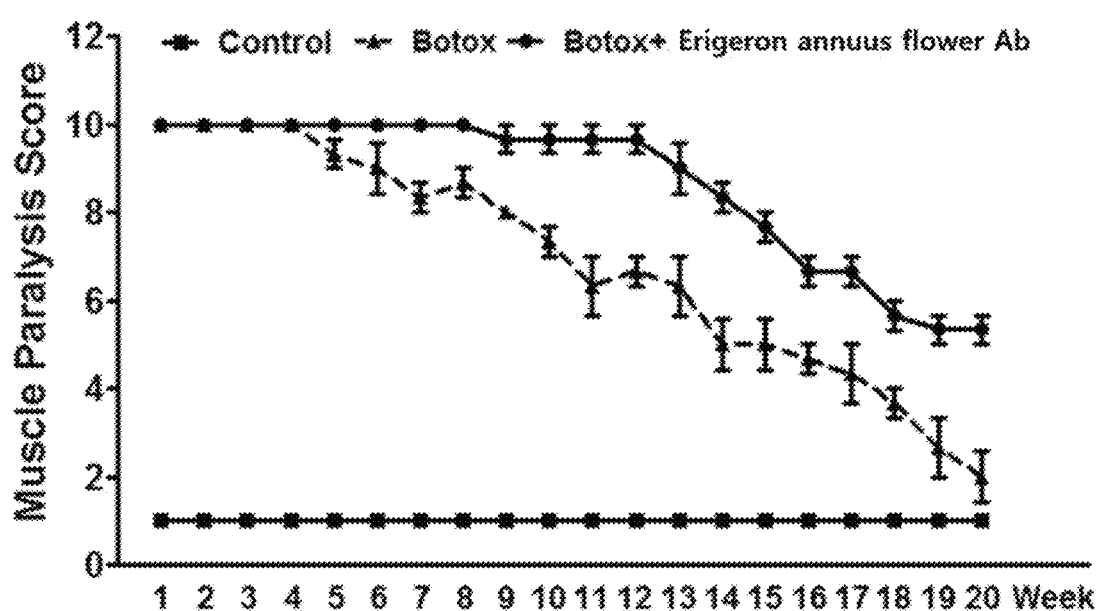

[FIG. 13]
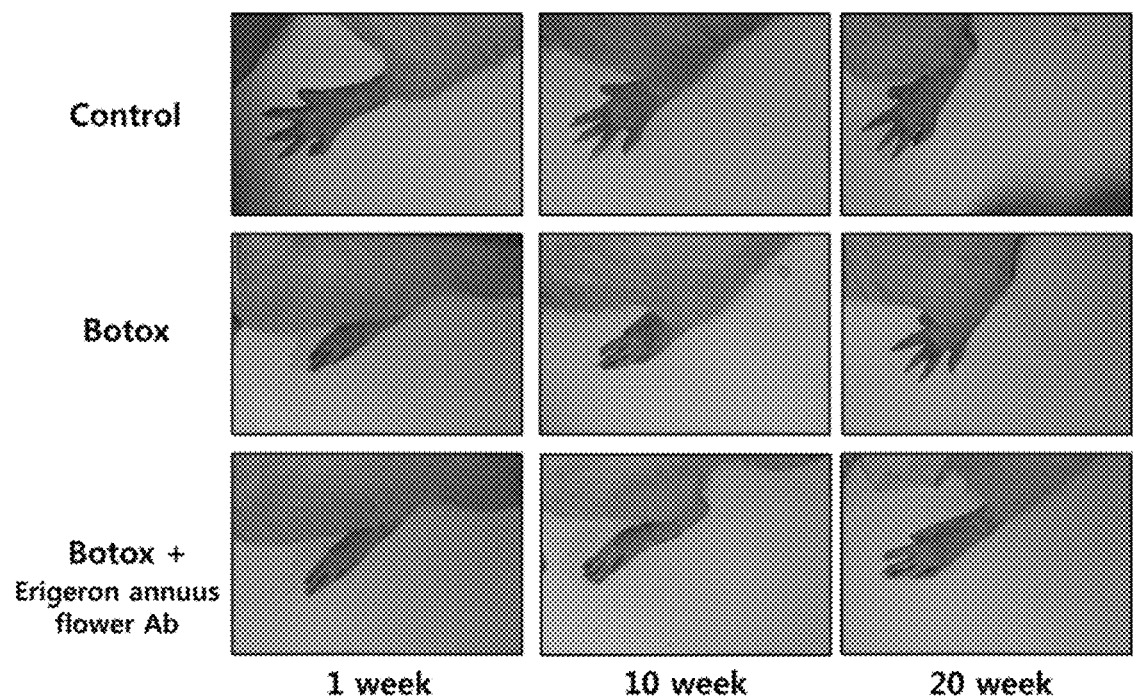

COMPOSITION COMPRISING ERIGERON ANNUUS FLOWER ESSENTIAL OIL FOR PREVENTION AND TREATMENT OF NEUROMUSCULAR DISEASE

CROSS-REFERENCE TO RELATED APPLICATIONS

This application is a National Stage of International Application No. PCT/KR2018/010592 filed Sep. 11, 2018, claiming priority based on Korean Patent Application No. 10-2018-0075159 filed Jun. 29, 2018, the entire disclosures of which are incorporated herein by reference.

TECHNICAL FIELD

The present disclosure relates to a pharmaceutical composition and a beauty-purposed pharmaceutical composition for prevention or treatment of neuromuscular disease, the composition containing a combination of Erigeron annuus flower-based essential oil and botulinum neurotoxin.

BACKGROUND ART

In release of a neurotransmitter, a synaptic vesicle containing the neurotransmitter must be fused with a presynaptic membrane to form a pathway between the two boundaries. In this connection, a protein that provides a fundamental force of the membrane fusion are a three-proteins complex called soluble N-ethylmaleimide-sensitive factor attachment protein receptors (SNARE).

The membrane fusion between the synaptic vesicle and the presynaptic membrane opens up a neurotransmitter release pathway. This involves a t-SNARE complex attached to a target membrane and a v-SNARE complex attached to the vesicle. The t-SNARE is a complex of a syntaxin 1a protein and a SNAP-25 (Synaptosomal-associated protein 25) protein. The v-SNARE is composed of a protein such as VAMP-2 (vesicle-associated membrane protein 2). The SNARE proteins are twisted to form a SNARE complex. In the membrane fusion, rearrangement of a lipid bilayer as well known in the art occurs. Since biological membranes are pushing strongly against each other, these membranes are not spontaneously fused with each other. Thus, a strong force from an outside is required to overcome the repulsion between the membranes. In this connection, the SNARE protein creates the strong force that may overcome the repulsion between the membranes. That is, the formation of the SNARE complex provides the force to overcome the repulsion between the membranes and involves extracellular exocytosis including the release of the neurotransmitter.

Reduction of the SNARE complex formation due to either destruction of the SNARE protein or expression inhibition thereof leads to inhibition of neuron terminal and vesicle membrane fusion, thus reducing neurotransmitter release. The contraction/relaxation of muscles is controlled by the release of neurotransmitters. Reducing the release thereof reduces muscle contraction, thereby inhibiting wrinkle generation due to the muscle contraction and reducing the produced wrinkles. Further, hyperhidrosis caused by excessive secretion of the neurotransmitter may be improved. Further, regarding skin's pores that are shrunk or enlarged by neuromodulation, selectively inhibiting a parasympathetic nerve may activate the sympathetic nerve due to a compensation action to contract muscles attached to the hair to shrink the skin's pores. Furthermore, when inhibiting the formation of mast cell-specific SNARE protein complex in vivo, degranulation of mast cells may be inhibited, such that allergic and autoimmune diseases may be treated and prevented.

Botulinum toxin as a representative substance that targets the SNARE is a toxin released from anaerobic bacteria of *Clostridium botulinum, C. butyricum, C. baratii* and *C. argentinense*. There are 7 types of botulinum toxin. Among them, botulinum toxin types A and B are purified and used medically. This toxin is a protease for cleaving the SNARE protein essentially involving in neurotransmitter excretion and is a main component of a drug known as botulinum neurotoxin.

The botulinum neurotoxin typically has the effect of causing paralysis by essentially blocking signals that cause muscle cramp or spasm. This muscle-paralysis effect is used for therapeutic effect. For example, the botulinum neurotoxin is used to treat diseases related to many neurotransmitter release-related and/or muscle-related diseases such as muscle tension, muscle cramp, hemifacial spasm, adult onset spasmodic torticollis, anal fissures, blepharospasm, facial muscle spasms, cerebral paralysis, headache, migraine, myalgia, strabismus, temperomandibular joint disorder, nerve pain, overactive bladder, urinary incontinence, rhinitis, sinusitis, acne, dystonia, dystonic spasm, hyperhidrosis, vocal cord disorder, myocardial disorder, etc. The botulinum neurotoxin is mainly used for the treatment for beauty purposes such as removing wrinkles, fine lines, frown lines, etc., and expanding the eyes, lifting oral angles, reducing muscle mass, and flattening a line extending from an upper lip. Specifically, the neurotoxin as the main component of botulinum neurotoxin may specifically act on the SNARE present in the neuron to cleave the SNARE protein to inhibit the complex formation to inhibit the membrane fusion to block the neurotransmitter release, thereby inhibiting muscle movement or sympathetic or parasympathetic nervous system. Thus, the botulinum neurotoxin shows therapeutic effects of the above diseases. However, the botulinum neurotoxin is a toxic substance and may have side effects. Further, the toxin complexes may induce the patient's immune system to form neutralizing antibodies. Thus, in order to achieve the same effect, higher doses of toxins are required in subsequent administrations. This requires a great deal of attention in determining the dosage or site of application.

Therefore, the present inventors have conducted studies to develop drugs that may increase the neurotransmitter release inhibition effect of botulinum neurotoxin, reduce cytotoxicity and improve stability. Thus, we confirmed that Erigeron annuus flower-based essential oil inhibits the reproduction of SNARE protein degraded by botulinum neurotoxin, thereby inhibiting neurotransmitter release and extending the duration of botulinum neurotoxin's effectiveness. In this way, the present disclosure has been completed.

DISCLOSURE

Technical Problem

Therefore, a purpose of the present disclosure is to provide a pharmaceutical composition and a beauty-purposed pharmaceutical composition for prevention or treatment of neuromuscular diseases, the composition containing a combination of Erigeron annuus flower-based essential oil and botulinum neurotoxin.

Another purpose of the present disclosure is to provide a beauty-purposed pharmaceutical composition containing a combination of Erigeron annuus flower-based essential oil and botulinum neurotoxin.

Further, still another purpose of the present disclosure is to provide a botulinum neurotoxin adjuvant containing Erigeron annuus flower-based essential oil as an active ingredient.

Further, still another purpose of the present disclosure is to provide a treatment method including administering, to a patient in need of neuromuscular disease treatment, a pharmaceutical composition containing a combination of Erigeron annuus flower-based essential oil and botulinum neurotoxin.

Further, still another purpose of the present disclosure a beauty-purposed treatment method including administering, to a subject in need of beauty-purposed treatment, a beauty-purposed pharmaceutical composition containing a combination of containing Erigeron annuus flower-based essential oil and botulinum neurotoxin.

Technical Solutions

In order to achieve the above purposes, the present disclosure provides a pharmaceutical composition for the prevention or treatment of neuromuscular diseases, the composition containing a combination of Erigeron annuus flower-based essential oil and botulinum neurotoxin.

Further, the present disclosure provides a beauty-purposed pharmaceutical composition containing a combination of Erigeron annuus flower-based essential oil and botulinum neurotoxin.

Furthermore, the present disclosure provides a botulinum neurotoxin adjuvant containing Erigeron annuus flower-based essential oil as an active ingredient.

Further, the present disclosure provides a treatment method including administering a pharmaceutical composition containing a combination of Erigeron annuus flower-based essential oil and botulinum neurotoxin to a patient in need of neuromuscular disease treatment.

Furthermore, the present disclosure provides a beauty-purposed treatment method including administering a beauty-purposed pharmaceutical composition containing a combination of Erigeron annuus flower-based essential oil and botulinum neurotoxin to a subject in need of beauty-purposed treatment.

Advantageous Effects

According to the present disclosure, Erigeron annuus flower-based essential oil inhibits t-SNARE protein and v-SNARE protein expression in neurons to inhibit the formation of SNARE protein complexes. Erigeron annuus flower-based essential oil inhibits the regeneration of t-SNARE protein and v-SNARE protein digested by botulinum neurotoxin to inhibit neurotransmitter release. Accordingly, an efficacy duration of botulinum neurotoxin may be extended. Thus, Erigeron annuus flower-based essential oil may be used in combination with botulinum neurotoxin as botulinum neurotoxin adjuvant for the prevention and treatment of neuromuscular disease or for beauty.

DESCRIPTION OF DRAWINGS

FIG. 1 is a schematic of the neurotransmitter release mechanism from neurons to muscle cells; (A) normal neurotransmitter release mechanism, (B) neurotransmitter release inhibition mechanism due to t-SNARE and v-SNARE degradation by botulinum neurotoxin (botulinum neurotoxin), (C) neurotransmitter release inhibition mechanism via t-SNARE and v-SNARE production inhibition by Erigeron annuus flower-based essential oil (Erigeron annuus flower Ab, Ab; absolute) in accordance with the present disclosure.

FIG. 2 shows a graph of the results of measuring viability (%) of neuron PC12 cells based on the treatment concentration of Erigeron annuus flower-based essential oil (Erigeron annuus flower Ab) in accordance with the present disclosure.

FIG. 3 shows the results of analysis of the protein expression of SNAP25, Syntaxin 1a, VAMP2 and Synaptotagmin-1 as SNARE proteins related to neurotransmitter release in PC12 cells based on treatment concentration of the Erigeron annuus flower-based essential oil (Erigeron annuus flower Ab) in accordance with the present disclosure.

FIG. 4 shows the inhibitory effect of formation of complexes of SNAP-25 and Syntaxin 1a proteins via inhibition of SNAP25 protein expression in PC12 cells based on treatment of Erigeron annuus flower-based essential oil (Erigeron annuus flower Ab) in accordance with the present disclosure.

FIG. 5 shows the measurement results of acetylcholine release amount (% of control) in PC12 cells based on the treatment of Erigeron annuus flower-based essential oil (Erigeron annuus flower Ab) in accordance with the present disclosure.

FIG. 6 shows the results of the measurement of norepinephrine release amount (% of control) in PC12 cells based on treatment with Erigeron annuus flower-based essential oil (Erigeron annuus flower Ab) in accordance with the present disclosure.

FIG. 7 shows the results of measuring dopamin release amount (% of control) in PC12 cells based on the treatment of Erigeron annuus flower-based essential oil (Erigeron annuus flower Ab) in accordance with the present disclosure.

FIG. 8 shows the results of measuring the cell viability (%) of L6 cells as the muscle cells, based on the treatment concentration of Erigeron annuus flower-based essential oil (Erigeron annuus flower Ab) in accordance with the present disclosure.

FIG. 9 shows the results of measuring cell viability (%) of rat aortic smooth muscle cells (RASMC) based on the treatment concentration of the Erigeron annuus flower-based essential oil (Erigeron annuus flower Ab) in accordance with the present disclosure.

FIG. 10 shows the results of protein expression of SNAP25, Syntaxin 1a and VAMP2 in L6 cells based on the treatment concentration of the Erigeron annuus flower-based essential oil (Erigeron annuus flower Ab) in accordance with the present disclosure.

FIG. 11 shows analysis results of the protein expression of SNAP25, Syntaxin 1a and VAMP2 in RASMC based on the treatment concentration of the Erigeron annuus flower-based essential oil (Erigeron annuus flower Ab) in accordance with the present disclosure.

FIG. 12 shows a graph of the results of analyzing thigh muscle paralysis of rats in control, botulinum neurotoxin treated group (botulinum neurotoxin) and botulinum neurotoxin and Erigeron annuus flower-based essential oil combined treated group (botulinum neurotoxin+Erigeron annuus flower Ab) over time (1 to 20 weeks).

FIG. 13 shows an image of the changes in the foot (leg) muscles of rats in control, botulinum neurotoxin treated group (botulinum neurotoxin), and botulinum neurotoxin and Erigeron annuus flower-based essential oil combined treated group (botulinum neurotoxin+Erigeron annuus flower Ab) over time (1, 10 and 20 weeks).

MODES OF THE INVENTION

Hereinafter, the present disclosure will be described in detail.

Pharmaceutical Composition and Beauty-Purposed Pharmaceutical Composition for Prevention or Treatment of Neuromuscular Disease The present disclosure relates to pharmaceutical compositions for the prevention or treatment of neuromuscular diseases, the composition containing Erigeron annuus flower-based essential oil and botulinum neurotoxin in combination with each other.

In the pharmaceutical composition according to the present disclosure, the botulinum neurotoxin may act to degrade the target membrane soluble N-ethylmaleimide-sensitive factor attachment protein receptor (t-SNARE) protein of the neuron membrane and the vesicle soluble N-ethylmaleimide-sensitive factor attachment protein receptor (v-SNARE) protein of the synaptic vesicle membrane. The Erigeron annuus flower-based essential oil may be responsible for inhibiting the regeneration of the t-SNARE protein and v-SNARE protein degraded by botulinum neurotoxin.

In the pharmaceutical composition according to the present disclosure, the Erigeron annuus flower-based essential oil may be extracted by an organic solvent extraction method using a volatile solvent. Preferably, the Erigeron annuus flower-based essential oil may be absolute (Ab) obtained by extracting the concrete by the organic solvent extraction method and extracting the concrete using alcohol to remove the insoluble wax therefrom to obtain the Ab.

Specifically, the absolute may be obtained by extracting the Erigeron annuus flower by the organic solvent extraction method using a volatile solvent to obtain concrete; and extracting the obtained concrete using alcohol to remove insoluble wax therefrom to obtain the absolute. The organic solvent extraction method and the method of separating the absolute from the extract may include any method that may be modified by one of ordinary skill in the art.

In general, regarding the normal neurotransmitter release mechanism from neurons to muscle cells, the neuron includes SNARE proteins including t-SNARE (a target membrane soluble N-ethylmaleimide-sensitive factor attachment protein receptor) attached to a neuron membrane (presynaptic membrane) as a target membrane, and v-SNARE (vesicle soluble N-ethylmaleimide-sensitive factor attachment protein receptor) attached to the membrane surface of the synaptic vesicle containing neurotransmitter such as acetylcholine in the neuron. The SNARE protein complex is formed via the combination of the t-SNARE and v-SNARE such that membrane fusion between the synaptic vesicle and the presynaptic membrane occurs to form a pathway between the two boundaries. This mechanism causes the neurotransmitter to be released into the muscle cell (see A of FIG. 1).

In this process, botulinum neurotoxin, that is, botulinum neurotoxin is administered to neuron such that botulinum neurotoxin molecules cleave and degrade the t-SNARE protein of the neuron membrane and the v-SNARE protein of the synaptic vesicles. This process inhibits the SNARE protein complex formation and prevents binding between the neuron membrane and synaptic vesicles to inhibit the neurotransmitter release (see B of FIG. 1).

When the Erigeron annuus flower-based essential oil according to the present disclosure is administered to neurons in which the t-SNARE protein and v-SNARE protein are degraded by botulinum neurotoxin, this may inhibit the expression of t-SNARE protein and v-SNARE protein in the neuron membrane and synaptic vesicles such that the two SNARE proteins may be inhibited from being regenerated. This inhibits the binding between the neuron membrane and synaptic vesicles, thereby inhibiting the release of neurotransmitters (see C of FIG. 1).

Therefore, when using Erigeron annuus flower-based essential oil in combination with botulinum neurotoxin, the above described mechanism may bring about the long-term efficacy of botulinum neurotoxin rather than when using botulinum neurotoxin alone.

In the pharmaceutical composition according to the present disclosure, the Erigeron annuus flower-based essential oil may extend the effectiveness period of botulinum neurotoxin by 1.5 to 10 times, preferably by 1.5 to 7 times, more preferably by 1.5 to 5 times.

In the pharmaceutical composition according to the present disclosure, the neuromuscular disease may be selected from the group consisting of muscle tension, muscle cramp, hemifacial spasm, adult onset spasmodic torticollis, anal fissures, blepharospasm, facial muscle spasms, cerebral paralysis, headache, migraine, myalgia, strabismus, temperomandibular joint disorder, nerve pain, overactive bladder, urinary incontinence, rhinitis, sinusitis, acne, pore dilatation, dystonia, dystonic spasm, hyperhidrosis, vocal cord disorder, myocardial disorder, etc. In addition, the neuromuscular disease may include a variety of muscle related diseases associated with alleviation or strengthening of immune response, or regulation of neurotransmitter release.

Further, the present disclosure relates to a beauty-purposed pharmaceutical composition containing a combination of Erigeron annuus flower-based essential oil and botulinum neurotoxin.

In accordance with the present disclosure, the beauty effect of the beauty-purposed pharmaceutical composition may be selected from the group consisting of a reduction in appearance of fine lines, a reduction in appearance of wrinkles, widening of the eyes, lifting the corner of the mouth, reduction of muscle mass and flattening of the lines that extends from the upper lip.

Botulinum Neurotoxin Adjuvant

The present disclosure relates to a botulinum neurotoxin adjuvant containing Erigeron annuus flower-based essential oil as an active ingredient.

In the botulinum neurotoxin adjuvant according to the present disclosure, the Erigeron annuus flower-based essential oil may inhibit re-production of t-SNARE (the target membrane soluble N-ethylmaleimide-sensitive factor attachment protein receptor) protein of the neuron membrane and the v-SNARE (vesicle soluble N-ethylmaleimide-sensitive factor attachment protein receptor) protein of the synaptic vesicle membrane as decomposed by the botulinum neurotoxin, thereby to extend the period for which the effects of botulinum neurotoxin including the SNARE protein complex formation inhibitory effect, neurotransmitter delivery effect, muscle paralysis effect, etc. may be maintained.

In one embodiment in accordance with the present disclosure, the thigh muscle paralysis of rats induced by botulinum neurotoxin lasts longer by at least two times in botulinum neurotoxin and Erigeron annuus flower-based essential oil combined treated group (botulinum neurotoxin+Erigeron annuus flower Ab) than in botulinum neurotoxin alone treated group (botulinum neurotoxin). Thus, the Erigeron annuus flower-based essential oil achieves the long-term efficacy of botulinum neurotoxin's neurotransmitter release inhibition (see Experimental Example 4, FIG. 12 and FIG. 13).

In accordance with the present disclosure, the botulinum neurotoxin adjuvant may be intended for the prevention or treatment of neuromuscular disease. The neuromuscular disease may be selected from the group consisting of muscle tension, muscle cramp, hemifacial spasm, adult onset spasmodic torticollis, anal fissures, blepharospasm, facial muscle spasms, cerebral paralysis, headache, migraine, myalgia, strabismus, temperomandibular joint disorder, nerve pain, overactive bladder, urinary incontinence, rhinitis, sinusitis, acne, pore dilatation, dystonia, dystonic spasm, hyperhidrosis, vocal cord disorder, myocardial disorder, etc. In addition, the neuromuscular disease may include a variety of muscle related diseases associated with alleviation or strengthening of immune response, or regulation of neurotransmitter release.

In accordance with the present disclosure, the botulinum neurotoxin adjuvant may be intended for beauty. The beauty effect may be selected from the group consisting of a reduction in appearance of fine lines, a reduction in appearance of wrinkles, widening of the eyes, lifting the corner of the mouth, reduction of muscle mass and flattening of the lines that extends from the upper lip.

The botulinum neurotoxin adjuvant according to the present disclosure may be administered concurrently with the botulinum neurotoxin. Alternatively, the botulinum neurotoxin adjuvant according to the present disclosure may be administered 1 to 6 weeks after administration of the botulinum neurotoxin, and preferably may be administered 1 to 4 weeks after administration of the botulinum neurotoxin.

Treatment Method of Neuromuscular Disease

The present disclosure provides a treatment method including administering a pharmaceutical composition containing the combination of Erigeron annuus flower-based essential oil and botulinum neurotoxin to patient in need of neuromuscular disease treatment.

In the treatment method according to the present disclosure, the botulinum neurotoxin may act to degrade t-SNARE (the target membrane soluble N-ethylmaleimide-sensitive factor attachment protein receptor) protein of the neuron membrane and v-SNARE (the vesicle soluble N-ethylmaleimide-sensitive factor attachment protein receptor) protein of the synaptic vesicle membrane. The Erigeron annuus flower-based essential oil may be responsible for inhibiting the regeneration of the t-SNARE protein and v-SNARE protein degraded by botulinum neurotoxin.

In the treatment method according to the present disclosure, the neuromuscular disease may be selected from the group consisting of muscle tension, muscle cramp, hemifacial spasm, adult onset spasmodic torticollis, anal fissures, blepharospasm, facial muscle spasms, cerebral paralysis, headache, migraine, myalgia, strabismus, temperomandibular joint disorder, nerve pain, overactive bladder, urinary incontinence, rhinitis, sinusitis, acne, pore dilatation, dystonia, dystonic spasm, hyperhidrosis, vocal cord disorder, myocardial disorder, etc. In addition, the neuromuscular disease may include a variety of muscle related diseases associated with alleviation or strengthening of immune response, or regulation of neurotransmitter release.

In the treatment method according to the present disclosure, the Erigeron annuus flower-based essential oil may be extracted by an organic solvent extraction method using a volatile solvent. Preferably, the Erigeron annuus flower-based essential oil may be absolute (Ab) obtained by extracting the concrete by the organic solvent extraction method and extracting the concrete using alcohol to remove the insoluble wax therefrom to obtain the Ab.

Specifically, the absolute may be obtained by extracting the Erigeron annuus flower by the organic solvent extraction method using a volatile solvent to obtain concrete; and extracting the obtained concrete using alcohol to remove insoluble wax therefrom to obtain the absolute. The organic solvent extraction method and the method of separating the absolute from the extract may include any method that may be modified by one of ordinary skill in the art.

In the treatment method according to the present disclosure, the Erigeron annuus flower-based essential oil may extend the effectiveness period of botulinum neurotoxin by 1.5 to 10 times, preferably by 1.5 to 7 times, more preferably by 1.5 to 5 times.

Beauty-Purposed Treatment Method

The present disclosure provides a beauty-purposed treatment method including administering a beauty-purposed pharmaceutical composition containing the combination of Erigeron annuus flower-based essential oil and botulinum neurotoxin to a subject in need of beauty-purposed treatment.

In the beauty-purposed treatment in accordance with the present disclosure, the beauty effect of the beauty-purposed pharmaceutical composition may be selected from the group consisting of a reduction in appearance of fine lines, a reduction in appearance of wrinkles, widening of the eyes, lifting the corner of the mouth, reduction of muscle mass and flattening of the lines that extends from the upper lip.

The present disclosure will be described in more detail with reference to the following Examples. However, the following Examples are only intended to embody the contents in accordance with the present disclosure and should not limit the present disclosure.

<Example 1> Preparation of Erigeron Annuus Flower-Based Essential Oil (Absolute)

Erigeron annuus flower-based essential oil was obtained from the flower of Erigeron annuus. Specifically, the Erigeron annuus flower was originated from the Erigeron annuus habitat in Asan, Chungnam. Erigeron annuus flower in the flowered state was collected, washed and extracted using organic solvent extraction.

That is, the not-dried Erigeron annuus flower was settled in hexane (n-hexane) and was extracted. We concentrated the extract by evaporating the hexane using rotary evaporation. Thus, a solid concrete was obtained. Then, the concrete was dissolved in ethyl alcohol and stored at $-20°$ C., and then insoluble wax was removed therefrom using vacuum cooling filtration. Then, Erigeron annuus flower-based essential oil (Erigeron annuus flower Ab, Ab; absolute) was prepared by separating/purifying ethanol using the rotary evaporator again. Then, the prepared Erigeron annuus flower-based essential oil was stored at a low temperature vessel of $4°$ C. and was used.

<Experimental Example 1> Analysis of SNARE Protein Expression in Neurons Based on Erigeron Annuus Flower-Based Essential Oil Treatment 1-1. Cytotoxicity Analysis to Neuron (PC12)

To determine the toxicity of Erigeron annuus flower-based essential oil (Erigeron annuus flower Ab) to neuron PC12, the viability of the PC12 cell based on treatment concentration of Erigeron annuus flower-based essential oil (Erigeron annuus flower Ab) was identified using XTT (2,3-bis[2-methoxy-4-nitro-5-sulfophenyl]-2H-tetrazolium-5-carboxanilide) analysis method.

Specifically, PC12 cells were dispensed in a 96 well microtiter plate so that the number of cells per well was set to $1.5 \times 10^4$ cells/100 µL/well and then, the plate was attached to 37° C., 5%, and $CO_2$ culturing device. After the culturing therein for 24 hours, Erigeron annuus flower-based essential oil (Erigeron annuus flower Ab) of Example 1 was diluted to each of concentrations of 0, 10, 20, 30, 40 and 50 µg/mL. Each diluted Erigeron annuus flower-based essential oil was added, at 100 µL, to each well. The cells were incubated for 36 hours. Ez-cytox and RPMI1640 were mixed with each other at a 1:1 ratio and then the mixture was added, at 20 µL, to each well and reacted for 30 minutes in the culturing device. We measured the absorbance at 450 nm using an ELISA plate reader (Synerge2, BioTek, USA). Then, the measurement was converted into a percentage. Thus, the results were obtained for the cytotoxicity of Erigeron annuus flower-based essential oil (Erigeron annuus flower Ab).

As a result, as shown in FIG. 2, it was confirmed that Erigeron annuus flower-based essential oil (Erigeron annuus flower Ab) of up to 50 µg/mL concentration exhibited no cytotoxicity.

1-2. SNARE Protein Expression Analysis

In order to determine the effect of Erigeron annuus flower-based essential oil (Erigeron annuus flower Ab) prepared in Example 1 on the expression of SNARE protein in neuron (PC12), the analysis was performed as follows.

Specifically, PC12 cells were cultured using RPMI1640 medium containing 10% fetal bovine serum. PC12 cells were injected into a 60 mm dish so that the number of cells per dish was $8 \times 10^5$ cells/60 mm dish and then the dish was attached at 37° C., 5%, and $CO_2$ culturing device. Erigeron annuus flower-based essential oil (Erigeron annuus flower Ab) was added to each dish at 0 to 50 µg/mL concentration. The cells were incubated for 36 hours. After cell lysis using cell lysis buffer, anti-SNAP25, anti-syntaxin 1a, anti-VAMP2 or anti-Syt-1 antibody and immunoblot were used to obtain results.

As a result, as shown in FIG. 3, all SNARE proteins related to neurotransmitter release, that is, SNAP25, Syntaxin 1a, VAMP2 and Syt-1 protein were inhibited in a concentration-dependent manner of Erigeron annuus flower-based essential oil (Erigeron annuus flower Ab).

1-3. SNARE Protein Complex Formation Analysis

In order to identify the effect of Erigeron annuus flower-based essential oil (Erigeron annuus flower Ab) prepared in Example 1 on the formation of SNARE protein complex in neuron (PC12), the experiment was conducted and analyzed as follows.

PC12 cells were cultured using RPMI1640 medium containing 10% fetal bovine serum. PC12 cells were injected into a 60 mm dish so that the number of cells per dish was $8 \times 10^5$ cells/60 mm dish and then the dish was attached at 37° C., 5%, and $CO_2$ culturing device. Erigeron annuus flower-based essential oil (Erigeron annuus flower Ab) was added to the dish at 50 µg/mL concentration. The cells were incubated for 36 hours. The PC12 cells were treated with K+ solution as SNARE complex inducer to induce the formation of SNARE complexes. After cell lysis using cell lysis buffer, the SNAP25 antibody was subjected to immunoprecipitation. Then, using anti-syntaxin 1a or anti-SNAP25 antibody and immunoblot, the test results were obtained.

As a result, as shown in FIG. 4, it was confirmed that the complex formation of SNAP25 and syntaxin 1a was inhibited by the treatment of Erigeron annuus flower-based essential oil (Erigeron annuus flower Ab).

<Experimental Example 2> Analysis of Neurotransmitter Release Inhibition Effect in Neuron Based on Erigeron Annuus Flower-Based Essential Oil Treatment 2-1. Acetylcholine Release Amount Analysis To determine the neurotransmitter release inhibitory effect of Erigeron annuus flower-based essential oil (Erigeron annuus flower Ab) on neuron (PC12), the release amount of neurotransmitter acetylcholine (acetylcholine) was measured using neuron (PC12) differentiated using NGF (Nerve Growth Factor).

Specifically, PC12 cells were cultured using RPMI1640 medium containing 10% fetal bovine serum. PC12 cells were injected into a 60 mm dish so that the number of cells per dish was $8 \times 10^5$ cells/60 mm dish and then the dish was attached at 37° C., 5%, and $CO_2$ culturing device. Erigeron annuus flower-based essential oil (Erigeron annuus flower Ab) was added to a dish at 25 and 50 µg/mL concentrations. The cell was incubated for 36 hours. NGF (Nerve Growth Factor) 50 ng/mL was added to the cultured PC12 cells which in turn were differentiated at 37° C., 5%, and $CO_2$ culturing device for 72 hours. After the differentiation, the cells were treated with K+ solution as the SNARE complex inducer to induce the SNARE complex formation and acetylcholine release. Then, a conditioned medium as a cell culture solution was collected in a tube and, then, using an acetylcholine analysis kit (Amplite, Calif., USA) was used to obtain the experiment results.

As shown in FIG. 5, the release of acetylcholine was significantly inhibited in both of Erigeron annuus flower-based essential oil (Erigeron annuus flower Ab) 25 and 50 µg/mL treated groups.

2-2. Norepinephrine Release Amount Analysis

In order to check the neurotransmitter release inhibitory effect of Erigeron annuus flower-based essential oil (Erigeron annuus flower Ab) on neuron (PC12), the samples were treated in the same manner as in above Experimental Example 2-1. The release amount of the neurotransmitter norepinephrine was measured using the norepinephrine assay kit (IBL international, Germany).

As a result, as shown in FIG. 6, it was confirmed that norepinephrine release was inhibited significantly in a concentration-dependent manner of the Erigeron annuus flower-based essential oil in the Erigeron annuus flower-based essential oil (Erigeron annuus flower Ab) treated group.

2-3. Dopamine Release Amount Analysis

To determine the neurotransmitter release inhibitory effect of Erigeron annuus flower-based essential oil (Erigeron annuus flower Ab) on neuron (PC12), the sample was treated in the same manner as the Experimental Example 2-1. The release amount of the neurotransmitter dopamine was measured using the dopamine Assay Kit (Demeditec, Germany).

As a result, as shown in FIG. 7, it was confirmed that the release amount of dopamine was significantly decreased in a concentration-dependent manner of the Erigeron annuus flower-based essential oil in the Erigeron annuus flower-based essential oil (Erigeron annuus flower Ab) treated group.

Therefore, Erigeron annuus flower-based essential oil (Erigeron annuus flower Ab) was able to inhibit the release of neurotransmitters acetylcholine, norepinephrine and dopamine.

<Experimental Example 3> Analysis of SNARE
Protein Expression in Muscle Cells and Rat Aortic
Smooth Muscle Cells Based on Erigeron Annuus
Flower-Based Essential Oil Treatment 3-1. Cytotoxicity Analysis to Muscle Cell (L6) and Rat Aortic Smooth Muscle Cell (RASMC)

To determine the toxicity of Erigeron annuus flower-based essential oil (Erigeron annuus flower Ab) to muscle cells (L6) and rat aortic smooth muscle cells (RASMC), the viability of muscle cells (L6) and rat aortic smooth muscle cells (RASMC) based on treatment concentration of Erigeron annuus flower-based essential oil (Erigeron annuus flower Ab) was identified using XTT (2,3-bis[2-methoxy-4-nitro-5-sulfophenyl]-2H-tetrazolium-5-carboxanilide) test.

Specifically, L6 or RASMC cells were dispensed in 96 well microtiter plates so that the number of cells per well was $5\times10^3$ cells/100 μL/well and the plate was attached at 37° C., 5%, and $CO_2$ culturing device. After the incubation, Erigeron annuus flower-based essential oil (Erigeron annuus flower Ab) of Example 1 was diluted to each of concentrations of 0, 0.1, 1, 10, 50 and 100 μg/mL and the diluted Erigeron annuus flower Ab was added, at 100 μL, to each well. Then, the cell was incubated for 24 hours. Then, Ez-cytox and DMEM were mixed with each other at 1:1 ratio, and the mixture was added, at 20 μL, to each well, followed by reaction for 30 minutes in a culturing device. The absorbance measurement at 450 nm using ELISA plate reader (Synerge2, BioTek, USA) was conducted. The absorbance measurement was expressed in terms of percentage. Thus, the results were obtained for the cytotoxicity of Erigeron annuus flower-based essential oil (Erigeron annuus flower Ab).

As a result, as shown in FIG. 8 and FIG. 9, it was confirmed that Erigeron annuus flower-based essential oil (Erigeron annuus flower Ab) of up to 50 μg/mL concentration exhibited no cytotoxicity to both of L6 cells and RASMC.

3-2. SNARE Protein Expression Analysis

To examine the effect of Erigeron annuus flower-based essential oil (Erigeron annuus flower Ab) prepared as in Example 1 on the expression of SNARE protein in muscle cells (L6) and rat aortic smooth muscle cells (RASMC), the test analysis was carried out as follows.

Specifically, L6 or RASMC was cultured using DMEM medium containing 10% fetal bovine serum. L6 or RASMC was injected into a 60 mm dish so that the number of cells per dish was $2\times10^5$ cells/60 mm dish and the dish was attached at 37° C., 5%, and a $CO_2$ culturing device. Erigeron annuus flower-based essential oil (Erigeron annuus flower Ab) was added to each dish at 0 to 50 μg/mL concentrations. The cells were incubated for 36 hours. After cell lysis using cell lysis buffer, anti-SNAP25, anti-syntaxin 1a or anti-VAMP2 antibody and immunoblot were used to obtain results.

As a result, as shown in FIG. 10 and FIG. 11, it was confirmed that unlike in the PC12 cell of the Experimental Example 1-2, in L6 and RASMC, changes in expressions of SNAP25, Syntaxin 1a and VAMP2 as SNARE proteins associated with neurotransmitter release did not occur.

Thus, from the same results, it was confirmed that Erigeron annuus flower-based essential oil (Erigeron annuus flower Ab) does not affect SNARE protein expression in muscle cells and rat aortic smooth muscle cells, but specifically inhibited the production of SNARE protein only in the neuron. Further, Erigeron annuus flower-based essential oil (Erigeron annuus flower Ab) does not have the effect of inhibiting transient neurotransmitter release by decomposing and eliminating t-SNARE protein or v-SNARE protein as already produced, which is a conventional effect of the botulinum neurotoxin. Rather, the Erigeron annuus flower-based essential oil (Erigeron annuus flower Ab) may inhibit the production of t-SNARE and v-SNARE in neuron, such that the neuron membrane and synaptic vesicles were prevented from binding to each other, thereby to inhibit the release of neurotransmitters such as acetylcholine, norepinephrine and dopamine.

<Experimental Example 4> Analysis of
Prolongation of Botulinum Neurotoxin Efficacy
Period Based on Erigeron Annuus Flower-Based
Essential Oil Treatment 4-1. Animal Model Preparation Specifically, 8-week-old Sprague-Dawley rats (Orient Bio) were used for animal experiments. Regarding botulinum neurotoxin used in the experiment, lyophilized botulinum neurotoxin (Xeomin, MERZ, Germany) was dissolved in 0.9% physiological saline at a concentration of 25 U/mL. Rats were classified into control, botulinum neurotoxin treated group (botulinum neurotoxin) and botulinum neurotoxin and Erigeron annuus flower-based essential oil combined treated group (botulinum neurotoxin+Erigeron annuus flower Ab).

First, saline solution, botulinum neurotoxin, and the combination of botulinum neurotoxin and Erigeron annuus flower-based essential oil (Erigeron annuus flower Ab) were administered to the left thigh muscle of the experimental animal. Samples were freshly administered to all treated groups at weekly intervals. 0.9% saline solution was administered to the control. 5 units of botulinum neurotoxin type A was administered to the botulinum neurotoxin treated group (botulinum neurotoxin) to cause paralysis of the left leg of the rat, and at a weekly interval, a solvent in which Erigeron annuus flower-based essential oil (Erigeron annuus flower Ab) was dissolved was administered thereto. 5 units of botulinum neurotoxin type A was administered to the botulinum neurotoxin and Erigeron annuus flower-based essential oil combined treated group (botulinum neurotoxin+Erigeron annuus flower Ab) to paralyze the left leg of the rat, and then, at a weekly interval, 50 μg/mL of Erigeron annuus flower-based essential oil (Erigeron annuus flower Ab) was administered thereto.

4-2. Analysis of Extension of Botulinum Neurotoxin Efficacy Period

To determine the effect of Erigeron annuus flower-based essential oil (Erigeron annuus flower Ab) on the extension of botulinum neurotoxin efficacy duration, the durations of thigh muscle paralysis in rats for the treated groups of the Experimental Example 4-1 were compared with each other based on visual observation analysis.

Specifically, the body weight and feed intake of rats in each of the treated groups were measured at 3 day intervals. Three observers observed the left foot of the rat at 1-week interval to measure the degree of muscle paralysis. In muscle paralysis analysis, the degree of muscle paralysis was divided into 0 to 10 points. According to the state of muscle paralysis, the score approximate to 10 was assigned when there is heavily paralyzed, whereas the score approximate to 0 was assigned when the paralysis is relieved.

As a result, as shown in FIG. 12 and FIG. 13, it was confirmed that, for the botulinum neurotoxin treated group (botulinum neurotoxin), the degree of the thigh muscle paralysis induced by the botulinum neurotoxin began to decrease after 5 weeks from the botulinum neurotoxin treatment, and, then, after 10 weeks therefrom, the degree of muscle paralysis decreased by half, and, then, after 20 weeks, little muscle paralysis remained. On the contrary, for botulinum neurotoxin and Erigeron annuus flower-based essential oil combined treated group (botulinum neurotoxin+Erigeron annuus flower Ab), the muscle paralysis degree was maintained to be the initial level for up to 12 weeks and then more than half of the degree muscle paralysis continued after 20 weeks.

That is, the rat thigh muscle paralysis period was significantly longer by at least two times in the botulinum neurotoxin and Erigeron annuus flower-based essential oil combined treated group (botulinum neurotoxin+Erigeron annuus flower Ab) than in the botulinum neurotoxin treated group (botulinum neurotoxin).

The above results indicate that t-SNARE and v-SNARE proteins are degraded by botulinum neurotoxin and at the same time, the production of the SNARE protein is inhibited by Erigeron annuus flower-based essential oil (Erigeron annuus flower Ab), such that the duration of the neurotransmitter release inhibition effect by the botulinum neurotoxin is extended. This has a significant impact on the therapeutic use of the composition containing the combination of Erigeron annuus flower-based essential oil (Erigeron annuus flower Ab) and botulinum toxin. In particular, using the composition according to the present disclosure may significantly reduce the frequency of subsequent botulinum neurotoxin administrations required to maintain the specific beauty or therapeutic effect previously caused by botulinum toxin. As a result, the reduced frequency of botulinum neurotoxin application may allow the subject to have the reduced tendency to produce antibodies to botulinum toxin, thereby resulting in better long-term efficacy.

The present disclosure has been described based on the preferred embodiments. Those of ordinary skill in the technical field to which the present disclosure belongs may understand that the present disclosure may be embodied in a modified form without departing from the essential characteristics in accordance with the present disclosure. Therefore, the disclosed embodiments should be considered in descriptive sense only and not for purposes of limitation. The scope of the present disclosure is set forth in the claims, not the foregoing description. All variations within the equivalent thereto shall be construed as included in the present disclosure.

The invention claimed is:

1. A beauty-purposed treatment method comprising administering a combination of Erigeron annuus flower-based essential oil and botulinum neurotoxin to a subject in need thereof,
   wherein the beauty-purposed treatment method is a method of providing a beauty effect selected from the group consisting of reduction in appearance of a fine line, reduction in appearance of a wrinkle, widening of an eye, lifting of a corner of a mouth, a reduction of muscle mass, and flattening of a line extending from an upper lip.

2. The beauty-purposed treatment method of claim 1, wherein the botulinum neurotoxin acts to degrade a target membrane soluble N-ethylmaleimide-sensitive factor attachment protein receptor (t-SNARE) protein of a neuron membrane, and a vesicle soluble N-ethylmaleimide-sensitive factor attachment protein receptor (v-SNARE) protein of a synaptic vesicle membrane, and
   wherein the Erigeron annuus flower-based essential oil acts to inhibit re-production of the t-SNARE protein and v-SNARE protein as degraded by botulinum neurotoxin.

3. The beauty-purposed treatment method of claim 1, wherein the Erigeron annuus flower-based essential oil extends an efficacy duration of the botulinum neurotoxin by 1.5 to 10 times.

* * * * *